(12) United States Patent
Dang et al.

(10) Patent No.: US 7,344,710 B2
(45) Date of Patent: Mar. 18, 2008

(54) COMBINATION BACTERIOLYTIC THERAPY FOR THE TREATMENT OF TUMORS

(75) Inventors: Long Dang, Ann Arbor, MI (US); Kenneth W. Kinzler, Bel Air, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 417 days.

(21) Appl. No.: 10/495,116

(22) PCT Filed: Nov. 21, 2002

(86) PCT No.: PCT/US02/37509

§ 371 (c)(1),
(2), (4) Date: Nov. 23, 2004

(87) PCT Pub. No.: WO03/045153

PCT Pub. Date: Jun. 5, 2003

(65) Prior Publication Data

US 2005/0079157 A1 Apr. 14, 2005

Related U.S. Application Data

(60) Provisional application No. 60/331,786, filed on Nov. 21, 2001.

(51) Int. Cl.
*A01N 63/00* (2006.01)
*A61K 48/00* (2006.01)

(52) U.S. Cl. .................. 424/93.1; 424/93.2; 424/93.41

(58) Field of Classification Search ............... 424/93.1, 424/93.2, 93.41
See application file for complete search history.

(56) References Cited

OTHER PUBLICATIONS

Brown, Martin J. et al., "The Unique Physiology of Solid Tumors: Opportunities (and Problems) for Cancer Therapy," *Cancer Research* (Apr. 1, 1998), pp. 1408-1416, vol. 58.
Cary, R.W. et al., "Clostridial Oncolysis in Man," *Europ. J. Cancer* (1987) pp. 37-46, vol. 3.
Clairmont, C. et al. "Biodistribution and Genetic Stability of the Novel Antitumor Agent VNP20009, a Genetically Modified Strain of *Salmonella typhimuriumj*," (2000), pp. 1996-2002, vol. 181.
Dang, Long H. et al., "Combination bacteriolytic therapy for the treatment of experimental tumors," www.pnas.org/cgi/dol/10,1073/pnas.251543698, Nov. 27, 2001.
Gericke, Dietmar et al., "Oncolysis by Clostridia. II. Experiments on a Tumor Spectrum with a Variety of Clostridia in Combination with Heavy Metals," *Cancer Research*, (Feb. 1964), pp. 217-221, vol. 24.
Kimura, Noritaka T. et al., "Selective Localization and Growth of *Bifidobacterium bifidum* in Mouse Tumors following Intravenous Administration," *Cancer Research*, (Jun. 1980), pp. 2061-2068, vol. 40.

Kohwi, Yoshinori et al., "Antitumor Effect of *Bifidobacterium infantis* in Mice," *Gann*, (Oct. 1978), pp. 613-618.
Lemmon, MJ et al., "Anaerobic bacteria as a gene delivery system that is controlled by the tumor microenvironment," *Gene Therapy*, (1997), pp. 791-796, vol. 4.
Low, K. Brooks et al., "Lipid A mutant *Salmonella* with suppressed virulence and TNFα induction retain tumor-targeting in vivo," *Nature Biotechnology*, (Jan. 1999) pp. 37-41, vol. 17.
Malmgren, Richard A. et al. Localization of the Vegetative Form of *Clostridium tetani* in Mouse Tumors Following Intravenous Spore Administration, *Cancer Research*, (1995), pp. 473-478.
Mose, J.R. et al., "Oncolysis by Clostridia. I. Activity of *Clostridium butyricum* (M-55) and Other Nonpathogenic Clostridia against the Ehrlich Carcinoma," *Cancer Research*, (Feb. 1964), pp. 212-216, vol. 24.
Parker, Raymond C. et al., "Effect of Histolyicus Infection and Toxin on Transplantable Mouse Tumors," *Proc. Soc. Exp. Biol. Med.*, (1947), pp. 461-467.
Schmassman, Adrian et al., "Cholecystokinin-B/gastrin receptors enhance wound healing in the rat gastric mucosa," *J. Clin. Invest.*, (Oct. 2000), pp. 1021-1029, vol. 106, No. 8.
Yazawa, Kazuyuki et al., "*Bifidobacterium longum* as a delivery system for gene therapy of chemically induced rat mammary tumors," *Breast Cancer Research and Treatment*, (2001), pp. 165-170, vol. 66.
Jeha S., "Tumor lysis syndrome," *Semin Hematol*,Oct. 2001; 38(4, Suppl 10):4-8 (Abstract only).
Martinez RD et al., Comparison of Clostridium sordellil toxins and LT with toxins A and B of C. difficile., *J Med Microbiol*, Jan. 1992; 36(1):30-6 (Abstract only).
Dang, Long H. Combination bacteriolytic therapy for the treatment of experimental tumors. Proceedings of the National Academy of Science. Dec. 18, 2001, vol. 98, No. 26, pp. 15155-15160, see entire document.

(Continued)

*Primary Examiner*—Mark Navarro
(74) *Attorney, Agent, or Firm*—Banner & Witcoff, Ltd.

(57) ABSTRACT

Current chemotherapeutic approaches for cancer are in part limited by the inability of drugs to destroy neoplastic cells within poorly vascularized compartments of tumors. We have here systematically assessed anaerobic bacteria for their capacity to grow expansively within avascutar compartments of transplanted tumors. Among 26 different strains tested, one (*Clostridium novyi*) appeared particularly promising. We created a strain of *C. novyi* devoid of its lethal toxin (*C. novyi*-NT) and showed that intravenously injected *C. novyi*-NT spores germinated within the avascular regions of tumors in mice and destroyed surrounding viable tumor cells. When *C. novyi*-NT spores were administered together with conventional chemotherapeutic drugs, extensive hemorrhagic necrosis of tumors often developed within 24 hours, resulting in significant and prolonged anti-tumor effects. This strategy, called combination bacteriolytic therapy (COBALT), has the potential to add a valuablle dimension to the treatment of cancer.

43 Claims, 6 Drawing Sheets

OTHER PUBLICATIONS

Eklund M W et al: "Relationship of bacteriophages to alpha toxin production in Clostridium novyi types A and B." Infection and Immunity. Sep. 1976, vol. 14, No. 3, pp. 793-803, XP002405800 ISSN: 0019-9567.

Eklund M W et al: "Interspecies conversion of clostridium botulinum type C to clostridium novyi type A by bacteriophage" SCIENCE 1974, vol. 186, No. 4162, 1974, pp. 456-458, XP002405801.

Minton N P et al: "Chemotherapeutic tumour targeting using clostridial spores" FEMS Microbiology Reviews, Elsevier, Amsterdam, NL, vol. 17, No. 3, 1995, pp. 357-364, XP002242524 ISSN: 0168-6445.

Minton N P et al: "Clostridia in Cancer Therapy" In: Bahl H and Dürre P Editors, Clostridia-Biotechnology and Medical Applications, Wiley-VCH, Weinheim, ISBN 3-527-30175-5, Feb. 15, 2001, pp. 251-270, XP001247867.

Theys J et al: "Improvement of Clostridium Tumour Tergetting Vectors Evaluated in Rat Rhabdomyosarcomas" FEMS Immunology and Medical Microbiology, Elsevier Science B.V., Amsterdam, NL, vol. 30, No. 1, Feb. 2001, pp. 37-41, XP001097591 ISSN: 0928-8244.

Hatheway C L: "Toxigenic clostridia."Clinical Microbiology Reviews. Jan. 1990, vol. 3, No. 1, 1, Jan. 1990, pp. 66-98, XP002408674 ISSN: 0893-8512.

*B. longum*        *C. novyi*

FIGURE 3

No Treatment      C. novyi-NT

US 7,344,710 B2

COMBINATION BACTERIOLYTIC THERAPY FOR THE TREATMENT OF TUMORS

This invention was made using U.S. government support from NIH grants CA 43460 and CA 62924. The U.S. government therefore retains certain rights in the invention.

TECHNICAL FIELD OF THE INVENTION

This invention is related to the field of oncology. In particular it relates to combined biological and chemical treatments of tumors.

BACKGROUND OF THE INVENTION

Despite enormous progress in understanding the pathophysiology of neoplasia, advanced forms of cancer remain recalcitrant to treatment. Though the basis for this failure is complex, one reason is that most tumors contain large, poorly vascularized areas that limit the efficacy of radiation and chemotherapeutic drugs (Jain, 1994)(Jain, 2001). The poorly vascularized regions are less sensitive to ionizing radiation because its cell-killing effects are dependent on oxygen; they are less sensitive to chemotherapeutic drugs because drug delivery to these regions is obviously suboptimal. As a cancer therapeutic agent must not leave significant clusters of viable cells within every lesion to achieve a clinically meaningful effect, the poorly vascularized regions of tumors represent a major obstacle to effective treatment.

One of the most important recent developments in tumor biology is the recognition that neoangiogenesis is essential for the growth of tumors to clinically meaningful sizes. What is less well-recognized is that this neoangiogenesis often does not keep pace with the growth of the neoplastic cells, resulting in large necrotic areas composed of dead or dying cells. For example, we found that each of 20 randomly selected liver metastases >1 cm$^3$ in size contained relatively large regions of necrosis/apoptosis, in general constituting 25% to 75% of the tumor mass (FIG. 1). Cells adjacent to these necrotic areas are poorly vascularized and likely to be difficult to treat with conventional agents.

It has been recognized for half a century that anaerobic bacteria can selectively proliferate in the hypoxic regions of tumors (Parker, 1947)(Malmgren, 1955)(Mose, 1963)(Gericke, 1963)(Thiele, 1963)(Carey, 1967)(Kohwi, 1978)(Brown, 1998)(Fox, 1996)(Lemmon, 1997)(Sznol, 2000)(Low, 1999)(Clairmont, 2000)(Yazawa, 2000)(Yazawa, 2001)(Kimura, 1980). Clever strategies for potentially exploiting such bacteria for diagnostic and therapeutic purposes have been devised, though relatively little work in this area has recently taken place.

SUMMARY OF THE INVENTION

One embodiment of the invention provides a method for treating tumors in a mammal. Spores of an anaerobic bacterium are administered to the mammal. A toxin gene of a wild type form of the anaerobic bacteriwn is deleted in the spores of the anaerobic bacterium, rendering the spores of the anaerobic bacterium less toxic to the mammal. An anti-tumor agent is also administered to the mammal. The tumor regresses or its growth is slowed or arrested as a result of these administrations.

Another embodiment of the invention provides a kit for treating tumors. The components of the kit are in a divided or undivided container. The components include spores of an anaerobic bacterium which is toxin-defective and an agent which collapses tumor vasculature.

Also provided by another embodiment of the present invention is an isolated and bacteriologically pure *Clostridium novyi* bacterium which is toxin-defective.

Still another embodiment of the invention provides an isolated and bacteriologically pure *Clostridium sordelii* bacterium which is toxin-defective.

These and other embodiments of the invention which will be apparent to those of skill in the art upon reading the specification provide the art with an exciting modality for treating patients with tumors.

BRIEF DESCRIPTION OF THE DRAWINGS

(FIG. 2A, FIG. 2B) High and low power view of representative *B. longum* experiment, showing bacteria (stained deep blue) clustered within a colony. (FIG. 2C) *C. novyi* experiment, showing dispersion of bacteria throughout the necrotic region of the tumor. (FIG. 2D) High power view, showing invasion of *C. novyi* bacteria into surrounding viable tumor cells (stained purple) on the left.

Figure 3:
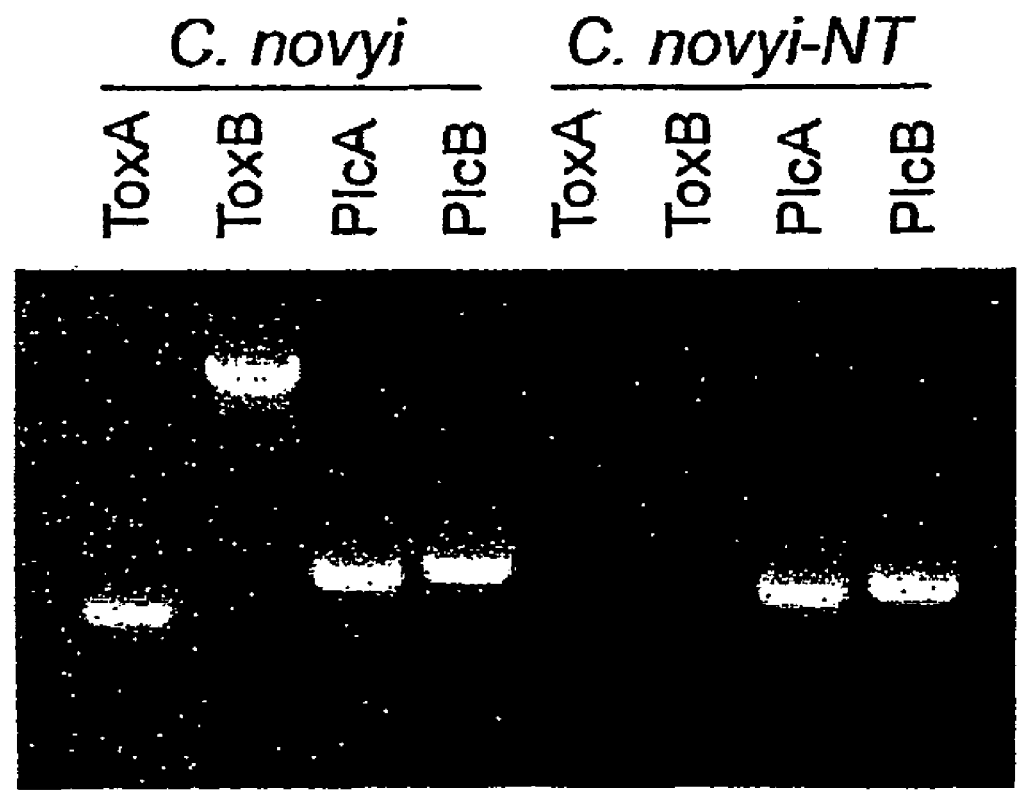

FIG. 3. Elimination of the lethal toxin gene from *C. novyi*. Following heat shock, PCR was performed on DNA from colonies to identify those which had lost the lethal toxin gene on the phage episome. Agarose gel electrophoresis of the PCR products with two independent primer sets (ToxA and ToxB) shows a *C. novyi* clone (*C. novyi*-N7) that had lost the gene and a clone (*C. novyi*) which retained them. Controls were provided by primer sets (PlcA and PlcB) specific for the *C. novyi* phospholipase C gene demonstrating the integrity of the DNA templates in all reactions.

FIG. 4A-4D. Distribution of *C. novyi*-NT bacteria after intravenous injection of spores.

(FIG. 4A) H & E stain of a typical HCT116 tumor xenograft from a mouse not injected with bacteria, showing some necrosis. (FIG. 4B) H & E stain of a tumor 24 hours following intravenous injection of $5\times10^7$ *C. novyi*-NT spores. (FIG. 4C) Gram stain, revealing bacteria distributed throughout the necrotic region. (FIG. 4D) High power view, showing a lawn of bacteria at the interface between the viable and necrotic regions of the tumor at the top and bottom of the picture, respectively.

FIGS. 5A -5B. Hemorrhagic necrosis following COBALT. (FIG. 5A) HCT116 tumor-bearing mouse 24 hours after iv injection with $5\times10^7$ *C. novyi*-NT spores. Slight swelling associated with edema is seen at the tumor site. D10 (0.3 mg/kg) was then given intravenously (time=0), and followed 24 hours later with MMC (4 mg/kg).

A black spot indicating hemorrhagic necrosis is evident near center of tumor at 0.3 days. The area of hemorrhagic necrosis gradually expanded over the next day. Swelling at the tumor site then resolved and the necrotic tumor mass and skin overlying it shrunk and gradually dissolved (days 6 to 30).

(FIG. 6A) HCT116 colorectal cancer cells were grown as xenografts in nude mice. When the tumors were ~700 mm$^3$ in size, the animals were injected intravenously with $5 \times 10^7$ C. novyi-NT spores (time 0), followed by iv injection with D10 (0.3 mg/kg) at 24 hours and ip injection with MMC (4 mg/kg) at 48 hours. Control groups were given no treatment or treated with D10 plus MMC without spores. Each group consisted of six to ten mice. Animals were euthanized when their tumors exceeded 15% of their body weight. In the experiment shown, seven of eight mice treated with a single dose of COBALT developed a striking hemorrhagic necrosis of their tumors within 24 hours after administration of D10. Four of these seven mice were cured, while three of the mice died three days after treatment, perhaps from tumor lysis syndrome (see Discussion). One mouse developed less extensive necrosis and its tumor eventually regrew. Only mice that survived treatment were used to obtain the data plotted in the graph. (FIG. 6B) Mice were treated as in (FIG. 6A), except that MMC was not used and treatments were given once every two weeks. (FIG. 6C) B16 melanoma cells were grown as subcutaneous syngeneic tumors in C57BL/6 mice. When the tumors were approximately 700 mm$^3$ in size, the animals were injected intravenously with $5 \times 10^7$ C. novyi-NT spores (time 0), followed by ip injection with CTX (100 mg/kg) at 6 hours and iv injection with D10 (0.3 mg/kg) at 24 hours. Other groups were given no treament, CTX plus D10, or spores plus D10. Each group consisted of at least ten mice and the treatments were repeated at weekly intervals. Four mice died after the first dose of COBALT and only those mice that survived treatment were used to obtain the data plotted in the graph. Animals were euthanized when their tumors exceeded 15% of body weight.

DETAILED DESCRIPTION

It is a discovery of the present inventors that combination bacteriolytic therapy (COBALT) can result in rapid and dramatic regressions of experimental tumors in mice. Even relatively large tumors could be treated successfully with COBALT, even though such tumors do not generally respond well to chemotherapeutic agents.

The bacteria useful in the practice of the present invention are anaerobic, spore formers. Suitable genera include *Bifidobacteria, Lactobacilli,* and *Clostridia*. A number of species of these bacteria have been tested for their ability to grow in tumors in a robust and dispersed manner. *Clostridium novyi* and *Clostridium sordelii* were found to be the best of the strains we tested for these properties. Other strains and species having suitable characteristics can be used as well.

Decreasing the natural production of toxins is desirable in using bacteria therapeutically. While strains need not be totally non-toxigenic, it is desirable that at least one of the toxin genes by mutated, deleted, or otherwise inactivated to render the bacteria less harmfull to the host. If a toxin gene is episomal or on a phage, then curing of the episome or phage can be used to delete the toxin gene. Techniques are well known in the art for mutagenesis and screening of mutants.

Isolated and bacteriologically pure vegetative bacteria or spores, according to the invention are those which are not contaminated with other bacteria or spores. Microbiological techniques for obtaining such pure cultures are will known in the art. Typically single colonies are picked and spread upon an agar nutrient medium, separating colonies so that new colonies arise that are the progeny of single cells. This process is typically repeated to ensure pure cultures. Alternatively, liquid cultnies can be serially diluted and plated for single colony formation. Serial repitition is desirable to enure colony formation from single cells. See, e.g., J. H. Miller, *Experiments in Molecular Genetics*, Cold Spring Harbor Laboratory, NY, 1972.

Figure 1:
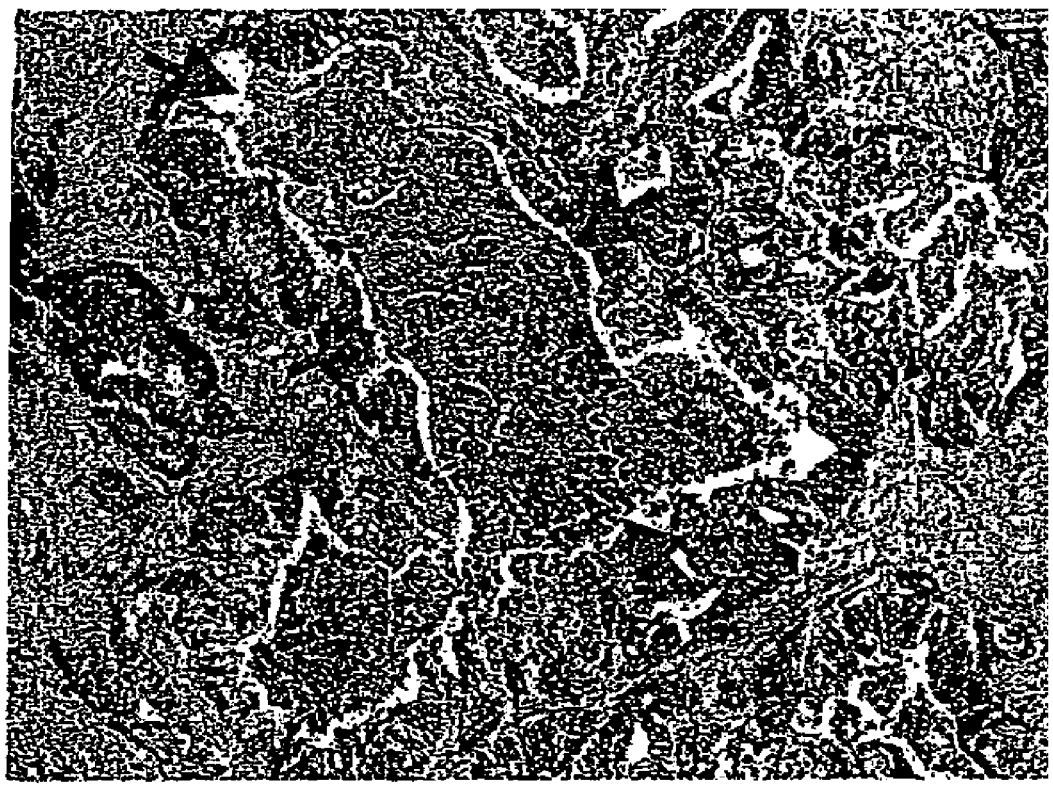
FIG. 1. Typical human colorectal metastases. Extensive areas of necrosis, indicated with arrows, are intermixed with areas of viable tumor cells. Similar large areas of necrosis were observed in each of the metastatic lesions from 20 different patients chosen at random from the pathologic archives.

Spores can be administered to a tumor-bearing mammal by any means which will afford access to the tumor. Spores can be injected intravenously, intradermally, subcutaneously, intramuscularly, intraperitoneally, intratrumorally, intrathecally, surgically, etc. Preferred techniques are intravenous and intratumoral injections. Tumor bearing mammals can be humans, pets, such as dogs and cats, agricultural animals such as cows, sheep, goats and pigs, and laboratory animals, such as rats, hamsters, monkeys, mice, and rabbits. The tumors to be treated are preferably large enough to have outgrown their blood supply and contain necrotic regions. This factor should not be limiting for most human tumor situations, as the great majority of clinically apparent human tumors have large necrotic regions within them (FIG. 1). However, micrometastatic disease might not be susceptible to COBALT.

Combination treatment involves administering anaerobic spores as well as a second anti-tumor agent. Together these agents synergize to produce a greater decerease in the growth of the tumor. Second anti-tumor agents which can be used include any which are known in the art. Such anti-tumor agents include but are not limited to DNA damaging agents, agents which collapse tumor vasculature, radiation, and anti-tumor antigen antibodies. These anti-tumor agents are administered according to the conventional means used in the art of medical and radiation oncology. The agents can be administered in any order or simultaneously. It may be desirable, however, to administer the spores prior to administering the second anti-tumor agent. If agents are to be administered serially, they are preferably administered within a span of a month, more preferably within a span of a fortnight, and even more preferably within a span of a week. Optimization of the time span is well within the skill of the art. Moreover, multiple anti-tumor agents can be administered in conjunction with the spores. Thus it may be desirable in order to achieve even greater reduction in tumor growth that a plurality of anti-tumor agents be used. Anti-tumor agents from different categories or mechanisms may achieve superior results. Thus a preferred combination includes spores, a tumor vasculature collapsing agent and a DNA damaging agent.

Suitable anti-tumor agents which function to collapse tumor vessels are vinblastine, vincristine, colchicine, combrestatin A-4, dolastatin-10, and 5,6 dimethylxanthenone-4-acetic acid. Others as are known or discovered with the same function can be used. Suitable DNA damaging chemotherapeutic drugs which can be used include but are not limited to mitomycin C and cytoxan.

In order to mitigate the side-effects of the anti-tumor therapy various additional drugs or therapies can be utilized.

These include allopurinol, hydration, uate oxidase, steroids such as prednisone, and hematopoietic factors such as granulocyte colony stimulating factor (G-CSF).

Kits comprising the useful components for practicing the anti-tumor methods of the present invention can be packaged in a divided or undivided container, such as a carton, bottle, ampule, tube, etc. The spores and anti-tumor agents can be packaged in dried, lyophilized, or liquid form. Additional components provided can include vehicles for reconsititution of dried components. Preferably all such vehicles are sterile and apyrogenic so that they are suitable for injection into a mammal without causing adverse reactions. The anti-tumor agents other than the spores are also preferably sterile. The spores are preferably microbiologically pure, i.e., containing no other bacteria other than the desired spore-forming anaerobe.

Treatment of mice with large tumors was sometimes toxic. Approximately 20% of mice with 350 mm$^3$ tumors and 50% of mice with 700 mm$^3$ tumors died within 24-72 hours of administration of spores plus D10. No deaths were observed after treatment with C. novyi-NT spores alone or with D10 alone. Though the basis for this toxicity is not yet known, it could have been due to efflux of toxic bacterial products from the tumors or due to "tumor lysis syndrome." It has previously been noted that the rapid lysis of very large tumor burdens is associated with systemic toxicity in humans treated with chemotherapy, perhaps due to the sudden efflux of tumor cell metabolites into the circulation (Altman, 2001). Though tumor lysis syndrome can be controlled in humans, it is difficult to control in mice. Any therapy which dramatically shrinks tumors may be subject to this side effect. Treatments for tumor lysis syndrome which may be used in humans include allopurinol, urate osidase, and volume repletion (hydration). Treatments to mitigate side-effects of anti-tumor agents such as bone marrow toxicity and neutropenia may also be desirable. Such treatment are will known in the art and can be employed here in the known manner.

The above disclosure generally describes the present invention. A more complete understanding can be obtained by reference to the following specific examples which are provided herein for purposes of illustration only, and are not intended to limit the scope of the invention.

EXAMPLE 1

In the work described below we attempted to exploit the fact that necrotic regions exist only within tumors and in no normal tissues. We wished to develop a toxic agent that could be specifically delivered to these areas and, in theory, could kill surrounding viable tumor cells. We chose to investigate anaerobic bacteria for this purpose. We hoped that a systematic screen for appropriate anaerobic bacteria that could kill tumor cells adjacent to the poorly vascularized regions, rather than just localize to such regions, would rejuvenate interest in this approach. Furthermore, we hoped that chemotherapeutic agents that killed the well-vascularized regions of tumors, when administered in conjunction with appropriate bacteria, would result in the destruction of a major proportion of neoplastic cells within the tumors.

We used the following materials and methods in our studies. Bacterial strains and growth. The bacterial strains tested in this study were purchased from the American Type Culture Collection and listed in Table 1. They were grown anaerobically in liquid cultures at 37° C. in Reinforced Clostridial Medium or Lactobacilli MRS broth (Difco, Detroit, Mich.).

Drugs. D10 (D10) was kindly provided by Dr. George R. Pettit (Cancer Research Institute, Arizona State University, AZ), Dr. Gregory P. Kalemkerian (Department of Internal Medicine, Wayne State University, MI), and Dr. Robert J. Schultz (Drug Synthesis and Chemistry Branch, NCI, Bethesda, Md.). Combretastatin A-4 was kindly provided by Dr. Robert J. Schultz. Cytoxan (CTX), mitomycin C (MMC), vincristine, colchicine, and vinblastine are commercially available chemotherapeutic agents (Sigma, St. Louis, Mo.).

Cell lines and animals. Female athymic nude and C57BL/6 mice 6 to 8 weeks of age were purchased from Harlan. HCT116 colon cancer cells and B16 melanoma cells were grown as monolayers in McCoy SA medium (Life Technologies, Rockville, Md.) supplemented with 5% fetal bovine serum and 1% penicillin/streptomycin (Cat. No. 15140-122).

Figure 2:
FIGS. 2A-2D. Distribution of anaerobic bacteria within tumors. Mice bearing subcutaneous B16 tumors were intravenously injected through the tail vein with 5×10$^7$ live *B. longum* bacteria or wild-type *C. novyi* spores. Mice with *B. longum* were given intraperitoneal injection with lactulose daily for five days to increase bacterial growth (Yazawa, 2000) and then sacrificed for analysis of tumor colonization. Mice with *C. novyi* were sacrificed the day after injection for analysis. Gram-stains revealed that a large number of *B. longum* bacteria was concentrated within a few colonies while *C. novyi* was dispersed throughout the poorly vascularized portions of the tumors.
Figure 2:
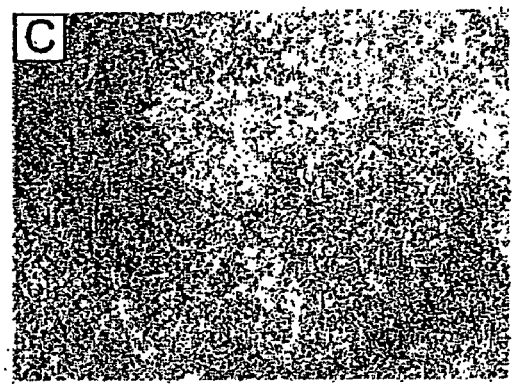
Figure 2:
Figure 2:
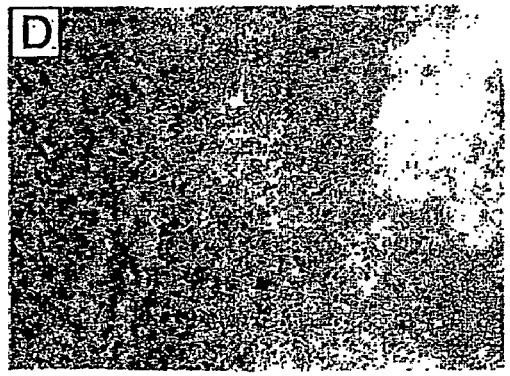
Figure 4:
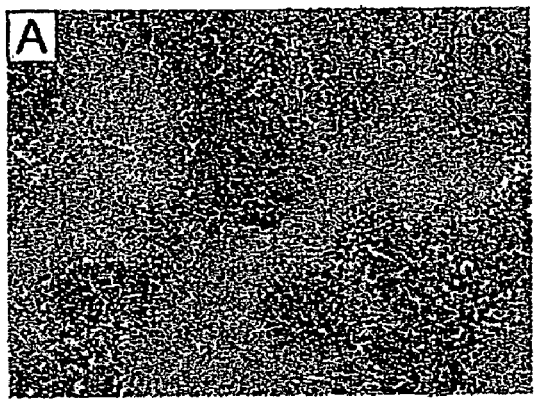
Figure 4:
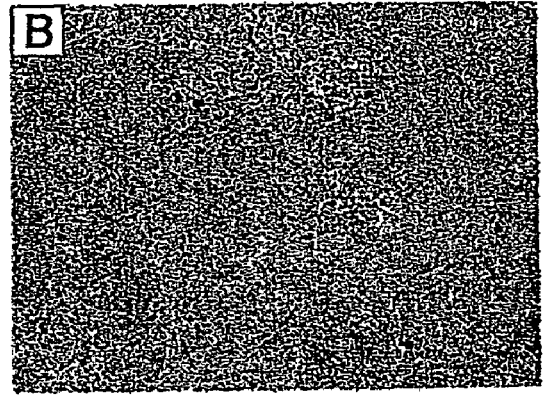

Sporulation and generation of nontoxigenic C. novyi strain. Spores of both wild-type and nontoxigenic C. novyi strains were generated by growing the organisms anaerobically at 37° C., pH 7.4 in a medium containing 5 g $Na_2HPO_4$, 30 g peptone, 0.5 L-cysteine, 10 g maltose and 5% w/v dried cooked meat particles (Difco, Detroit, Mich.) per 1 liter. After one week in this medium, spores settled in the cooked meat particle layer (Bagadi, 1973). Spores were further purified from contaminating vegetative forms on a discontinuous Percoll gradient. To remove the lethal toxin gene from the wild type *C. novyi* strain, *C. novyi* spores were heated at 70° C. for 15 minutes to inactivate the phage carrying the toxin (Eklund, 1974 )(Eklund, 1976). The spores were then plated on RCM agar and incubated anaerobically at 37° C. for 48 hours. Isolated colonies were cultured in liquid RCM for another 24 to 48 hours and then tested for the presence of the lethal toxin gene by PCR. In general, 1% of the bacterial colonies were found to lose the phage carrying this gene.

In vivo studies. Six to eight week old female Balb/c athymic nude or C57BL/6 mice were implanted with subcutaneous tumors through the injection of $2.5\times10^6$ HCT116 or B16 cells, respectively. After 8 to 12 days of tumor establishment, treatment was initiated with spores or drugs. Screening of bacterial strains for their ability to populate tumor grafts was done by either intratumoral injection (100 ul volume, $1\times10^7$ bacteria) or intravenous injection (500 ul volume, $5\times10^7$ bacteria or spores) of the tail vein. *C. novyi*-NT spores and D10 were diluted to the appropriate concentration in 1×Dulbecco's phosphate-buffered saline pH 7.4 (PBS) (Life Technologies, Rockville, Md.) and then administered by intravenous injection in a volume of 500 ul. CIX and MMC were diluted in PBS and then given by intraperitoneal injection in a volume of 500 ul. Tumor growth was assessed by measuring the size of the major and minor axes of subcutaneous tumors every two and every four days for B16 and HCT116 tumors, respectively, using calipers. Tumor volume was then calculated using the equation length×width$^2$×0.5.

EXAMPLE 2

Choice Of Bacterial Species. From previous studies it was clear that species of anaerobic bacteria could grow within the hypoxic regions of tumors. An example is provided by *B. longum*, which, when injected intravenously into mice with subcutaneous tumors, grew specifically and robustly within the tumors but not within normal tissues (Yazawa, 2000)(Yazawa, 2001). Gram stains of sections of the tumors, however, revealed that most bacteria were tightly clustered within colonies rather than distributed throughout the necrotic regions (FIG. 2A, FIG. 2B). As we considered dispersion of the bacteria essential to achieve the desired effects, numerous anaerobic species of three different genera were tested in an effort to find one(s) exhibiting this phenotype (Table 1). For this purpose, *Bifidobacterium* and *Lactobacillus* strains were injected intravenously, while *Clostodium* strains, which are generally highly toxic when injected intravenously, were injected directly into tumors. Among the 26 strains listed in Table 1, only two (*C. novyi* and *C. sordellii*) exhibited extensive spreading throughout the poorly vascularized portions of the tumors (not shown). Though this spread was undoubtedly facilitated by the motile nature of these two species, other motile anaerobic bacteria, including other *Clostridium* strains, did not exhibit this property when tested under identical conditions.

TABLE 1

Bacterial strains tested

*Bifidobacteria*

| | |
|---|---|
| B. adolescentis | ATCC 15703 |
| B. animalis | ATCC 25527 |
| B. bifidum | ATCC 11863, 15696 |
| B. boum | ATCC 27917 |
| B. breve | ATCC 15700 |
| B. coryneforme | ATCC 25911 |
| B. dentium | ATCC 15423, 27534 |
| B. indicum | ATCC 25912 |
| B. infantis | ATCC 15702, 25962 |
| B. longum | ATCC 15707 |
| B. magnum | ATCC 27540 |
| B. pseudolongum | ATCC 25526 |

*Lactobacilli*

| | |
|---|---|
| L. bifidus | ATCC 11146 |
| L. delbruecki ATCC 21815 | |

*Clostridia*

| | |
|---|---|
| C. absonum | ATCC 27555 |
| C. acetobulylicum | ATCC 824 |
| C. bifermentans | ATCC 17836 |
| C. difficile | ATCC 700057 |
| C. histolyticum | ATCC 19401 |
| C. novyi | ATCC 19402 |
| C. perfringens | ATCC 3624, 13124 |
| C. sordellii | ATCC 9714 |

EXAMPLE 3

Infiltration of the Tumor Mass Following Intravenous Injection of *C. novyi* spores. In order for an experimental therapy to represent a potentially viable tool for the treatment of disseminated cancers, it must have the capacity to be delivered systemically rather than through local, intratumoral injection. Though live bacteria are often toxic when injected intravenously, it has been shown that bacterial spores are non-toxic to normal animals. Accordingly, we found that large numbers (up to $10^8$ in a volume of 500 ul) of *C. novyi* and *C. sordellii* spores could be injected intravenously into normal mice without causing any noticeable side effects. When intravenously injected into mice with subcutaneous B16 tumors, however, the *C. novyi* bacteria floridly germinated within the tumors within 16 hours (FIG. 2C). In contrast, no germinated bacteria were observed in the liver, spleen, kidney, lung, or brain of these mice (not shown). Similar results were observed after iv injection of *C. sordellii* spores (not shown).

EXAMPLE 4

Genetic modification of *C. novyi*. Though *C. novyi* and *C. sordellii* spores both had the capacity to grow within tumors and kill some surrounding tumor cells, there was at least one small problem encountered with this experimental treatment: 16 to 18 hours following the initiation of treatment, all the mice died. We suspected that the cause of death was the release of potent lethal toxins from the bacteria germinating within the tumors. Indeed, other anaerobic bacterial spores have proved highly toxic to animals and humans following germination within the anaerobic environments present in tumors or wounds, and the resultant mortality shown to be due to specific secreted toxins (Boyd, 1972)(Boyd, 1972) (Bette, 1991)(Rood, 1991)(Bryant, 2000).

To mitigate systemic toxicity, we attempted to eliminate the lethal toxin gene from *C. novyi*. We chose *C. novyi* rather than *C. sordellii* for this purpose because the latter has two homologous toxin genes (Martinez, 1992) rather than one and because the single *C. novyi* toxin gene is located within a phage episome (Eklund, 1974)(Eklund, 1976)(Hofmann, 1995). Bacteria were heat treated to induce loss of the phage and inoculated onto agar plates. Of 400 bacterial colonies screened, three were observed to have lost the toxin gene when assessed by PCR using toxin-gene specific primers (examples in FIG. 3). Phospholipase C, a *C. novyi* gene contained within the bacterial rather than the phage genome (Tsutsui, 1995), served as control for this PCR experiment. One clone, named *C. novyi*-NT, that had lost the toxin gene, was selected for further analysis.

EXAMPLE 5

Destruction of Tumor Cells Following Injection of *C. novyi*-NT spores. *C. novyi*-NT spores devoid of the lethal toxin were injected intravenously into mice with tumors. These spores retained their capacity to germinate within tumors and resulted in greatly expanded areas of necrosis (FIG. 4A vs. FIG. 4B). However, these spores, unlike those of their parents, were non-toxic when injected alone, with no ill effects generally observed after injection of up to $10^8$ spores into mice with tumors. In contrast, all mice died after injection of $5\times10^7$ parental *C. novyi* spores into mice with tumors. Growing bacteria could be observed throughout the much-enlarged necrotic regions of tumors after injection of spores (FIG. 4C, FIG. 4D). The enlargement of the necrotic regions was apparently due to the destruction of viable tumor cells adjacent to the original necrotic regions by the bacteria. Indeed, a bacterial “film” (McManus, 1982) was routinely observed at the interface between the necrotic area and the remaining viable rim of the tumor, as if the bacteria were destroying the viable tumor cells and using its degradation products as nutrients (FIG. 4D). This tumor infiltration effect was similar to that observed with wild-type *C. novyi* bacteria (FIG. 2D).

EXAMPLE 6

Combination Therapy. We hoped to combine a bacterial agent with more conventional chemotherapeutic agents in an effort to attack the tumors from both the inside and outside, respectively. Following preliminary investigations with several such agents, we concentrated on two classes: (i) DNA damaging agents, such as MMC and CTX, which selectively kill tumor cells, and (ii) agents that appear to partially collapse tumor vasculature, such as flavone acetic acid derivatives and microtubule binding agents (Chaplin, 1996)

(Sweeney, 2001). The latter class of agents has been shown to be able to interfere with proper circulation through the tumors and thereby trap large molecules, such as antibodies or bacteria, that have gained access to the tumor tissue (Theys, 2001)(Pedley, 1999)(Pedley, 2001). Among flavone acetic acid and the microtubule-binding agents tested (including vinblastine, vincristine, colchicine, combretastatin A-4, and D10), D10 appeared to have the most pronounced effects and was chosen for further experimentation.

Figure 5:
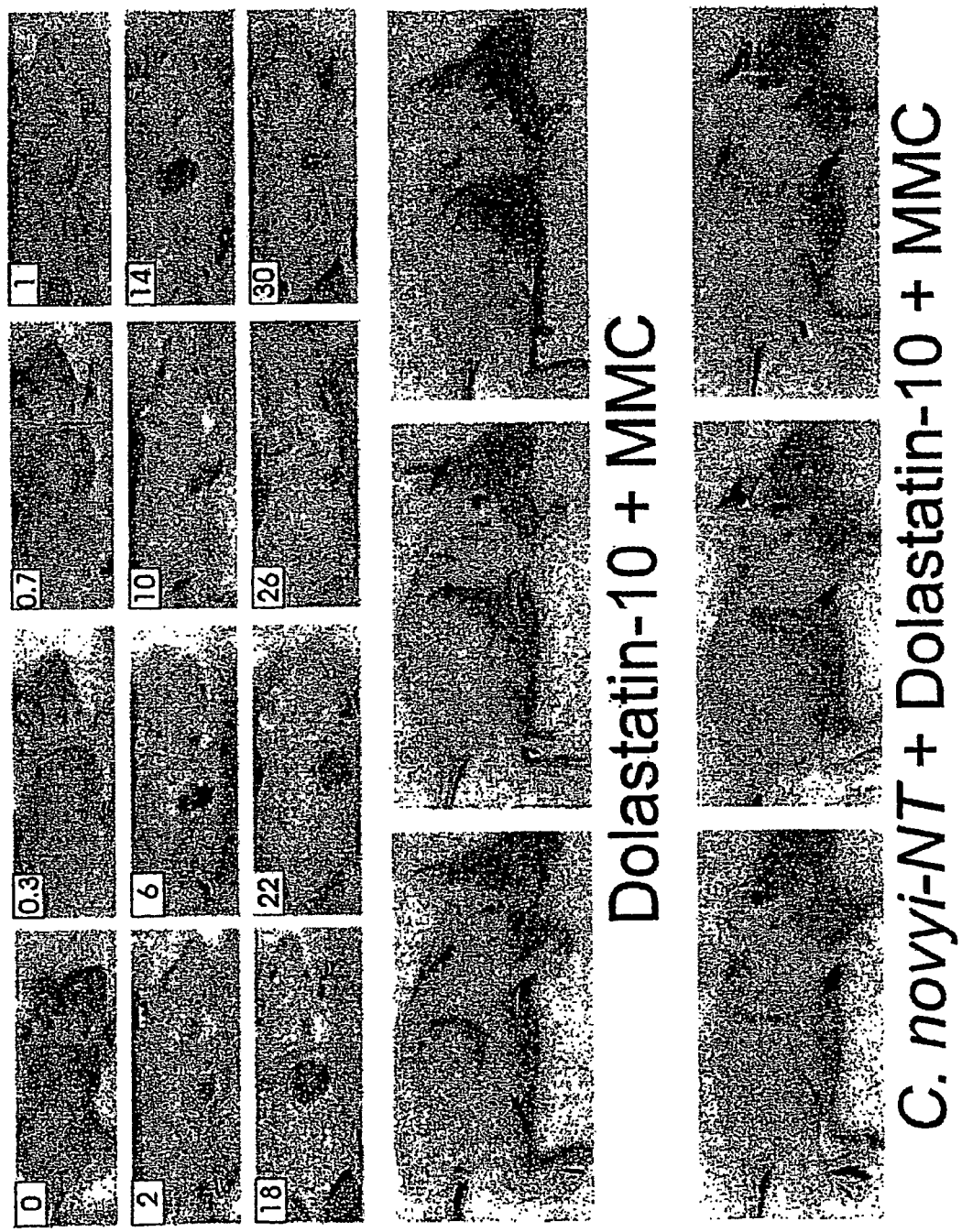
(FIG. 5B) Typical mice five weeks after treatment with a single dose of D10 plus MMC (top) or with a single dose of COBALT (bottom). Of the eight mice treated with COBALT in this experiment, four were apparently cured of their tumor, as no recurrence was observed after three months of observation.

Xenografts of the colorectal cancer cell line HCT116 were used to test the effects of this combination therapy in nude mice, as the tumors could easily be visualized under the hairless skin. As shown in FIG. 5, sequential treatment with C. novyi-NT spores, D10 and MMC resulted in dramatic effects on large subcutaneous tumors (starting tumor volume ~700 mm$^3$), easily observable through the skin. Twenty four hours following the injection of C. novyi-NT spores, the tumor mass swelled and became edematous (FIG. 5A). Six hours after receiving D10, a black spot developed near the center of the tumor, representing an area of hemorrhagic necrosis. This spot expanded in size and within 24 hours often completely enveloped the tumor (FIG. 5A, 1 day time point). H & E staining of sections of these tumors revealed extensive destruction of the tumors, often accompanied by infiltration of inflammatory cells. These necrotic masses then shrank over a period of two to four weeks (FIG. 5A, 14-30 day time points). In many mice, these necrotic masses eventually dissolved and disappeared, leaving the animals tumor-free (FIG. 5B). Similar, though less dramatic results, were observed following the sequential treatment with C. novyi-NT and D10 (without MMC), but never with D10 and MMC in the absence of C. novyi-NT and rarely with C. novyi-NT alone.

Figure 6:
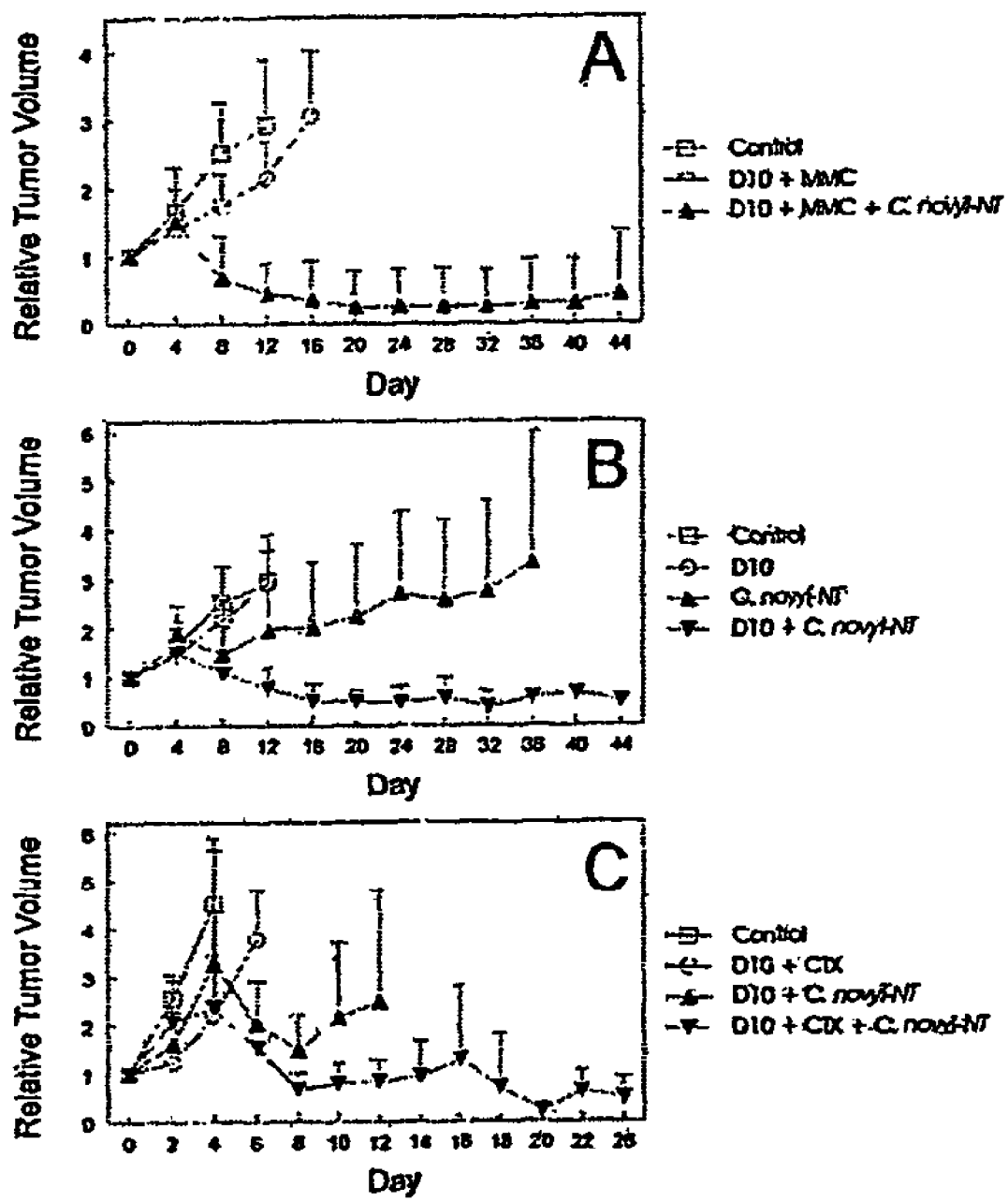
FIGS. 6A-6C. Quantitation of the Effects of COBALT.

The anti-neoplastic effects of this combination bacteriolytic therapy (COBALT) were further quantified in the experiments shown in FIG. 6. Animals with relatively large subcutaneous HCT116 tumors (starting tumor volume ~700 mm$^3$) were treated with drugs alone (D10 plus MMC) or C. novyi-NT spores plus the drugs. As can be seen in FIG. 6A, the drugs alone slowed the growth of the tumors, though the tumors continued to grow and the animals had to be sacrificed at ten to fourteen days, when tumor weights exceeded 10% of body weight. The addition of C. novyi-NT spores dramatically enhanced the effects of treatment, with tumors actually shrinking rather than simply slowing. In the experiment shown in FIG. 6A, four of eight animals had complete tumor regressions after only one administration of COBALT. Significant tumor shrinkage was also seen when mice were given sequential treatment with C. novyi-NT spores plus D10 (FIG. 6B). However, there was no long-term tumor-free survival and the treatment had to be repeated once every two weeks unless the full combination, with MMC, was included. Systemic treatment with C. novyi-NT spores alone slowed tumor growth while D10 alone had no effect, clearly illustrating the value of the combination (FIG. 6B).

To determine whether COBALT would affect other tumor types, we treated C57BL/6 mice with large syngeneic B16 tumors. In this case, CTX was substituted for MMC, as B16 tumor cells were more sensitive to CTX than to MMC. As shown in FIG. 6C, the drugs alone had some anti-tumor effects, as expected, though the tumor continued to grow in size and the animals had to be sacrificed within a week after beginning therapy. C. novyi-NT spores considerably enhanced these effects, and the tumors remained small over the four week course of this experiment. As with HCT116 human tumors, we found that D10 plus C. novyi-NT spores had significant anti-neoplastic effects on B16 tumors, but that the addition of a tumor cytotoxic agent (CTX) further enhanced the efficacy of COBALT (FIG. 6C). In the B16 tumor model, maintenance COBALT (once weekly) was required to keep tie tumors from regrowing while with HCT116 cells, a single treatment cured ~half the mice.

The results recorded above show that COBALT can result in rapid and dramatic regressions of experimental tumors in mice. Even relatively large tumors could be treated successfully with COBALT, though tumors of the size used in our experiments don't generally respond well to chemotherapeutic agents (FIGS. 6A-6C).

It is also clear that many questions remain. For example, we don't understand the basis for the potent tumor cell killing in the vicinity of the germinating bacteria. We found that many other bacterial strains could germinate within the necrotic regions of tumors but did not exhibit this potent cytotoxic activity. This killing is clearly not due to the lethal toxin gene of C. novyi, as this gene was deleted in the C. novyi-NT strain used in COBALT. It will be interesting in the future to determine which of the C. novyi-NT genes are responsible for these tumor cytolytic effects.

Another point of interest was that an agent acting on the vasculature (D110) was synergistic with the C. novyi-NT spores in causing significant tumor shrinkage. Presumably, the vascular collapse further lowered the oxygen tension near the trapped bacteria and thereby increased the potential for bacterial growth. D10 was given after the bacterial spores rather than before because we believed that partial vascular collapse prior to spore administration might have a deleterious effect on spore delivery. This belief was based on the fact that other vascular collapsing agents, such as DMXAA and combretastatin A-4, have been shown to exert their effects in combination with radioactively labeled antibodies only when administered after, and not before the antibodies (Theys, 2001)(Pedley, 1999)(Pedley, 2001).

REFERENCES

1. Altman, A. (2001) *Semin. Oncol.* 28, 3-8
2. Bagadi, H. O. & Sewell, M. M. (1973) *Res. Vet. Sci*, 15, 53-61
3. Bette, P., Okshe, A., Mauler, F., von Eichel-Streiber, C., Popoff, M. R. & Habemmann, E. (1991) *Toxicon* 29, 877-887
4. Boyd, N. A., Walker, P. D. & Thomson, R. O. (1972) *J. Med. Microbiol.* 5, 459-465
5. Boyd, N. A., Thomson, R. O. & Walker, P. D. (1972) *J. Med. Microbiol.* 5, 467-472
6. Brown, J. M. & Giaccia, A. J. (1998) *Cancer Res.* 58, 1408-1416
7. Bryant, A. E., Chen, R. Y., Nagata, Y., Wang, Y., Lee, C. H., Finegold, S., Guth, P. H. & Stevens, D. L. (2000) *J. Infect. Dis.* 182, 799-807
8. Carey, R. W., Holland, J. F., Whang, H. Y., Neter, E. & Bryant, B. (1967) *Eur. J Cancer* 3, 37-46
9. Chaplin, D. J., Pettit, G. R., Parkins, C. S. & Hill, S. A. (1996) *Br. J. Cancer* 27, Suppl., S86-S8
10. Clairmont, C., Lee, K. C., Picke, J., Ittensohn, M., Low, K. B., Pawelek, J., Bermudes, D., Brecher, S. M., Margitich, D., Turiier, J., et al. (2000) *J. Infect. Dis.* 181, 1996-2002
11. Eklund, M. W., Poysky, F. T., Meyers, J. A. and Pelroy, G. A. (1974) *Science* 186, 456-458
12. Eklund, M. W., Poysky, F. T., Peterson, M. E. & Meyers, J. A. (1976) *Infect. Immun.* 14, 793-803

13. Folkman, J. (2000) in Cancer Medicine, ed. Frei, J. F. H. a. E. (B. C. Decker, Hamilton, ON, Canada), pp. 132-152

14. Fox, M. E., Lemmon, M. J., Mauchline, M. L., Davis, T. O., Giaccia, A. J., Minton, N. P. & Brown, J. M. (1996) Gene Ther. 3, 173-178

15. Gericke, D. & Engelbart, K (1963) *Cancer Res.* 217-221
16. Hofmann, F., Hemnann, A., Habermann, E. & von Eichel-Streiber, C. (1995) *Mol. Gen. Genet.* 247, 670-679
17. Jain, R. K. (2002) *Adv. Drug Delivery Ref.* 46, 149-168

18. Kimura, N. T., Taniguchi, S., Aoki, K. & Baba, T. (1980) *Cancer Res.* 40,2061-2068

19. Kohwi, Y., Imai, K., Tamura, Z. & Hashimoto, Y. (1978) *Gann* 69, 613-618
20. Lemmon, M. J., van Ziji, P., Fox, M. E., Mauchline, M. L., Giaccia, A. J., Minton, N. P. & Brown, J. M. (1997) *Gene Ther.* 4, 791-796
21. Low, K. B., Ittensohn, M., Le, T., Platt, J., Sodi, S., Amoss, M., Ash, O., Cannichael, E., Challroborty, A., et al. (1999) *Nat. Biotechnol.* 17, 37-41
22. Malmgren, R. A. & Flanigan, C. C. (1955) *Cancer Res.* 125, 473-478
23. Martinez, R. D. & Wilkins, T. D. (1992) *J. Med. Microbiol.* 36, 30-36
24. McManus, A. T., McLeod, C. G., Jr., & Mason, A. D., Jr. (1982) *Arch. Surg. (Chicago)* 117, 187-191
25. Mose, J. R. & Mose, G. (1963) *Cancer Res.* 24, 212-216
26. Parker, R. C., Plunmner, H. C., Siebenmann, C. O. & Chapman, M. G. (1947) *Proc. Soc. Exp. Biol. Med.* 66, 461
27. Pedley, R. B., Shannan, S. K., Boxer, G. M., Boden, R., Stribbling, S. M., Davies, L., Springer, C. J. & Begent, R. H. (1999) *Cancer Res.* 59, 3998-4003
28. Pedley, R. B., Hill, S. A., Boxer, G. M., Flynn, A. A., Boden, R., Watson, R., Dearling J., Chaplin, D. J. & Begent, R. H. (2001) *Cancer Res.* 61, 4716-4722
29. Rood, J. E. & Cole, S. T. (1991) *Microbiol. Rev.* 55, 621-648
30. Sweeney, C. J., Miller, K. D., Sissons, S. E., Nozaki, S., Heilman, D. K., Shen, J. & Sledge, G. W., Jr. (2001) *Cancer Res.* 61, 3369-3372
31. Sznol, M., Lin, S. L., Bermudes, D., Zheng, L. M. & King, I. (2000) *J. Clin. Invest.* 106, 1027-1030
32. Thiele, E. H., Arison, R. N. & Boxer, G. E. (1963) *Cancer Res.* 24, 222-231
33. Tsutsui, K., Minami, J., Matsushita, O., Katayama, S., Taniguchi, Y., Nakamura, S., Nishioka, M. & Okabe, A. (1995) *J. Bacteriol.* 177, 7164-7170
34. Theys, J., Landuyt, W., Nuyts, S., Van Mellaert, L., Bosmans, E., Rijinders, A., Van Den Bogaert, W., van Oosterom, A., Anne, J. & Lambin, P. (2001) *FEMS Immunol. Med. Microbiol.* 30, 37-41

35. Yazawa, K., Fujimori, M., Amano, J., Kano, Y. & Taniguchi, S. (2000) *Cancer Gene Ther.* 7,269-274

36. Yazawa, K., Fujimori, M., Nakamura, T., Sasaki, T., Amano, J., Kano, Y. & Taniguchi, S. (2001) *Breast Cancer Res. Treat.,* 66, 165-170

The invention claimed is:

1. A method for treating a tumor in a mammal, comprising:
administering to the mammal spores of an isolated and bacteriologically pure *Clostridium novyi* bacterium which is toxin-defective, whereby the tumor regresses or its growth is slowed or arrested.

2. A method for treating a tumor in a mammal, comprising:
administering to the mammal spores of an isolated and bacteriologically pure *Clostridium sordeili* bacterium which is toxin-defective, whereby the tumor regresses or its growth is slowed or arrested.

3. A method for treating a tumor in a mammal comprising:

administering to the manunal spores of an anaerobic bacterium in which a toxin gene of a wild type form of the anaerobic bacterium is deleted, rendering the spores of the anaerobic bacterium less toxic to the mammal; and administering to the mammal an anti-tumor agent;

whereby the tumor regresses or its growth is slowed or arrested, and wherein the anaerobic bacterium is *Clostridium novyi* or *clostridium sordellii.*

4. The method of claim 3 wherein the spores are administered intravenously.

5. The method of claim 3 wherein the spores are administered intratumorally.

6. The method of claim 3 wherein the anti-tumor agent is radiation.

7. The method of claim 3 wherein the anti-tumor agent is an antibody.

8. The method of claim 3 wherein the anti-tumor agent collapses tumor vasculature.

9. The method of claim 8 wherein the spores are administered intravenously.

10. The method of claim 8 wherein the spores are administered intratumorally.

11. The method of claim 8 wherein the anti-tumor agent is vinblastine.

12. The method of claim 8 wherein the anti-tumor agent is vincristine.

13. The method of claim 8 wherein the anti-tumor agent is colchicine.

14. The method of claim 8 wherein the anti-tumor agent is combretastatin A-4.

15. The method of claim 8 wherein the anti-tumor agent is dolastatin-10.

16. The method of claim 8 wherein the anti-tumor agent is 5,6 dimethylxanthenone-4-acetic acid.

17. The method of claim 8 further comprising:

administering a DNA damaging chemotherapeutic drug.

18. The method of claim 17 wherein the DNA damaging chemotherapeutic drug is mitomycin C.

19. The method of claim 17 wherein the DNA damaging chemotherapeutic drug is cytoxan.

20. The method of claim 3 wherein the spores and anti-tumor agent are administered serially.

21. The method of claim 17 wherein the spores and agent and DNA damaging chemotherapeutic drug are administered serially.

22. A method for treating a tumor in a mammal comprising:

intravenously administering to the mammal spores of a *Clostridium novyi* bacterium which is toxin-defective;

administering dolastatin-10 to the mammal;

whereby the tumor regresses or its growth is slowed or arrested.

23. A method for treating a tumor in a mammal comprising:

intravenously administering to the mammal spores of a *Clostridium novyi* bacterium which is toxin-defective;

administering dolastatin-10 to the mammal; and administering cytoxan to the mammal;

whereby the tumor regresses or its growth is slowed or arrested.

24. The method of claim 3 further comprising:

administering allopurinol to the mammal.

25. The method of claim 3 further comprising: hydrating the mammal.

26. The method of claim 3 further comprising: administering urate oxidase to the mammal.

27. The method of claim 8 further comprising: administering allopurinol to the mammal.

28. The method of claim 8 further comprising: hydrating the mammal.

29. The method of claim 8 further comprising: administering urate oxidase to the mammal.

30. The method of claim 8 further comprising: administering a steroidal agent to the mammal.

31. The method of claim 30 wherein the steroidal agent is prednisone.

32. The method of claim 8 further comprising: administering G-CSF to the mammal.

33. The method of claim 17 further comprising: administering allopurinol to the mammal.

34. The method of claim 17 further comprising: hydrating the mammal.

35. The method of claim 17 further comprising: administering urate oxidase to the mammal.

36. The method of claim 17 further comprising: administering a steroidal agent to the mammal.

37. The method of claim 36 wherein the steroidal agent is prednisone.

38. The method of claim 17 further comprising: administering G-CSF to the mammal.

39. The method of claim 1 wherein the bacterium is cured of an episome which comprises a gene encoding the toxin.

40. The method of claim 2 wherein the bacterium is cured of an episome which comprises a gene encoding the toxin.

41. The method of claim 3 wherein the bacterium is cured of an episome which comprises a gene encoding the toxin.

42. The method of claim 22 wherein the bacterium is cured of an episome which comprises a gene encoding the toxin.

43. The method of claim 23 wherein the bacterium is cured of an episome which comprises a gene encoding the toxin.

* * * * *